US00PP29768P2

(12) United States Plant Patent
Bacon

(10) Patent No.: US PP29,768 P2
(45) Date of Patent: Oct. 23, 2018

(54) GRAPEVINE PLANT NAMED 'SUGRAFIFTYTHREE'

(50) Latin Name: *Vitis vinifera*
Varietal Denomination: Sugrafiftythree

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 15/732,444

(22) Filed: Nov. 13, 2017

(51) Int. Cl.
*A01H 5/08* (2018.01)

(52) U.S. Cl.
USPC ..... Plt./205

(58) Field of Classification Search
USPC ..... Plt./205
See application file for complete search history.

*Primary Examiner* — Annette H Para
(74) *Attorney, Agent, or Firm* — Knobbe, Martens, Olson & Bear, LLP

(57) ABSTRACT

A new and distinct grapevine variety 'Sugrafiftythree' is characterized by an early ripening, broad elliptic, dark-red berry, and a large berry and cluster weight. The berries of 'Sugrafiftythree' are very firm.

1 Drawing Sheet

Latin name of the genus and species claimed: *Vitis vinifera.*

Variety denomination: 'SUGRAFIFTYTHREE'.

BACKGROUND AND SUMMARY OF THE INVENTION

This application relates to the discovery and asexual propagation of a new and distinct variety of grapevine, 'Sugrafiftythree', as herein described and illustrated. The new variety was first selected as breeder number 'GR604R' by Terry A. Bacon in Wasco, Kern County, Calif. in July 2016. The variety was originated by controlled hybridization.

The new variety 'Sugrafiftythree' is characterized by broad, elliptic, early ripening, dark-red berries, having a large berry and cluster weight. The berries of 'Sugrafiftythree' are very firm.

The seed parent is the varietal selection '04006-199-045' (unpatented) and the pollen parent is the varietal selection 'GR363W' (unpatented breeding selection). The parent varieties were first crossed in April 2014. The date of first sowing was March 2015, and the date of first flowering was April 2016.

The new variety 'Sugrafiftythree' was first asexually propagated in December 2016 in Wasco, Kern County, Calif., by Terry A. Bacon using hardwood cuttings.

The new variety 'Sugrafiftythree' differs from its seed parent '04006-199-045' in that the new variety has red berries compared to green berries for '04006-199-045'.

The new variety 'Sugrafiftythree' differs from its pollen parent 'GR363W' (unpatented) in that the new variety has red berries compared to green berries for 'GR363W'.

The new variety 'Sugrafiftythree' has a similar red berry color as 'Flame Seedless' (unpatented), but the berries of the new variety 'Sugrafiftythree' have a broad elliptic shape compared to a round shape for 'Flame Seedless'. The new variety 'Sugrafiftythree' has a similar red berry color as 'Sheegene-12' (U.S. Plant Pat. No. 20,252), but ripening of the berries of the new variety 'Sugrafiftythree' starts about June 29 compared to about August 1 for 'Sheegene-12'.

The new 'Sugrafiftythree' variety has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration shows typical specimens of the foliage and fruit of the present new grape variety 'Sugrafiftythree'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three-year-old 'Sugrafiftythree' plants grown in the vicinity of Wasco, Kern County, Calif. during 2017, and is believed to apply to plants of the variety grown under similar conditions of soil and climate elsewhere.

VINE

General: (Measurements taken on a three year old plant).
- *Vine size.*—Large. Height: Approximately 2.0 m. Width: Approximately 2.5 m.
- *Vigor.*—Vigorous.
- *Density of foliage.*—Dense.
- *Productivity.*—Very productive.
- *Crop load.*—Approximately 28 kg per vine after thinning.
- *Own root.*—Yes.
- *Training method.*—Typically spur pruned leaving 2 bud spurs.
- *Resistance.*—Average resistance and susceptibility to diseases or pests of *Vitis vinifera* species.

Trunk:
- *Shape.*—Stocky.
- *Diameter.*—Approximately 7.5 cm (at 30 cm above the soil line).
- *Straps.*—Short.
- *Surface texture.*—Medium shaggy.
- *Inner and outer bark color.*—Inner bark about Medium Greyed-Orange 166C and Medium Greyed-Green 197B in outer bark.

SHOOTS

Young shoot:
- *Form of tip.*—Half open.
- *Intensity of anthocyanin coloration of tip.*—Absent or very weak.
- *Density of prostrate hairs on tip.*—Absent or very sparse.
- *Density of erect hairs on tip.*—Absent or very sparse.
- *Color.*—About Medium Green 139C.

Woody shoot (observations made in the middle third of shoot):
- *Attitude before tying.*—Semi-drooping.
- *Growth of axillary shoots.*—Medium strong, mainly 17 cm to 21 cm.
- *Internode length.*—Medium, Approximately 120 mm.
- *Width at node.*—Approximately 13 mm.
- *Cross section.*—Circular.
- *Surface texture.*—Striated.
- *Main color.*—About Medium Greyed-Orange 166C.
- *Color of dorsal side of internode.*—About Medium Greyed-Orange 166C.
- *Color of ventral side of internode.*—About Medium Greyed-Orange 166C.
- *Color of dorsal side of node.*—About Medium Greyed-Orange 166C with Dark Greyed-Orange 166A around the bud.
- *Color of ventral side of node.*—About Medium Greyed-Orange 166C with Dark Greyed-Orange 166A around the bud.
- *Density of erect hairs on nodes.*—Absent or Very Sparse.
- *Density of erect hairs on internodes.*—Absent or Very Sparse.
- *Density of prostrate hairs on internodes.*—Absent or Very Sparse.
- *Density of prostrate hairs on nodes.*—Absent or Very Sparse.

Tendrils:
- *Distribution on the shoot at full flowering.*—Discontinuous.
- *Thickness.*—Approximately 4 mm.
- *Color.*—About Light Yellow-Green 148D in mid-summer.
- *Form.*—Bifurcated.
- *Number of consecutive tendrils.*—Up to 2.
- *Length of tendril.*—Medium, approximately 15 cm to 19 cm.

LEAVES

Young leaves:
- *Color of upper surface of first 4 distal unfolded leaves.*—About Medium Green 138B.
- *Average intensity of anthocyanin coloration of six distal leaves prior to flowering.*—Absent.
- *Density of prostrate hairs between veins at lower surface of 4th distal unfolded leaf.*—Absent or very sparse.
- *Density of erect hairs between veins at lower surface of 4th distal unfolded leaf.*—Absent or very sparse.
- *Density of prostrate hairs on veins at lower surface of 4th distal unfolded leaf.*—Absent or very sparse.
- *Density of erect hairs on veins at lower surface of 4th distal unfolded leaf.*—Absent or very sparse.

Mature leaves (observations made in the middle third of shoot):
- *Average length.*—Large, approximately 15 cm.
- *Average width.*—Large, approximately 15 cm.
- *Shape of blade.*—Pentagonal.
- *Number of lobes.*—Approximately 5.
- *Mature leaf profile.*—Undulate.
- *Blistering surface of blade upper surface.*—Absent or very weak.
- *Leaf blade tip.*—In the plane of the leaf.
- *Undulation of margin.*—Slight.
- *Thickness.*—Average — typical of *Vitis vinifera* species.
- *Overall shape of teeth.*—Mixture of both sides straight and both sides convex.
- *Length of teeth.*—Medium, ranging from about 4 mm to 10 mm.
- *Ratio length/width of teeth.*—Very small, nearly 1:1.
- *General shape of petiole sinus lobes.*—Generally slightly open, some closed.
- *Tooth at petiole sinus.*—Absent.
- *Petiole sinus limited by veins.*—Absent.
- *Shape of upper lateral sinus lobes.*—Usually slightly open, some closed.
- *Depth of upper lateral sinuses.*—Deep, approximately 3 cm to 4 cm.
- *Density of prostrate hairs between veins on lower surface of blade.*—Absent to very sparse.
- *Density of erect hairs between veins on lower surface of blade.*—Absent to very sparse.
- *Density of prostrate hairs on main veins on lower surface of blade.*—Absent to very sparse.
- *Density of erect hairs on main veins on lower surface of blade.*—Absent to very sparse.

*Density of prostrate hairs on main veins on upper surface of blade*.—Absent to very sparse.

*Autumn coloration of leaves*.—Usually about Medium Green 138B, becoming Medium Grey-Brown 199C.

Upper leaf surface:

*Color*.—About Dark Green 139A.

*Surface texture*.—Smooth, dull.

*Surface appearance*.—Dull.

*Anthocyanin coloration of main veins*.—Absent or very sparse.

Lower leaf surface:

*Color*.—About Medium Yellow-Green 146B.

*Surface texture*.—Smooth, dull.

*Surface appearance*.—Dull.

*Anthocyanin coloration of main veins*.—Absent or very sparse.

Petiole:

*Length of petiole*.—Approximately 5 cm.

*Diameter*.—Approximately 3 mm.

*Length of petiole compared to middle vein*.—Much shorter, 5 cm for the petiole compared to 11 cm for middle vein.

*Density of prostrate hairs on petiole*.—Absent.

*Density of erect hairs on petiole*.—Absent.

*Color*.—About Medium Yellow-Green 147C.

Buds:

*Shape*.—Conical.

*Size*.—Medium, approximately 3 mm wide × 4 mm long.

*Position*.—Slightly held out.

*Bud fruitfulness*.—Basal, mostly fruitful 5th to 7th bud position.

*Time of bud burst*.—Medium, approximately March 10th for the southern San Joaquin Valley, Calif. region.

FLOWERS

General:

*Flower type*.—Fully developed stamen and fully developed gynoecium.

*Position of first flowering node*.—Usually $4^{th}$ to $5^{th}$ node of current season growth.

*Number of inflorescences per shoot*.—Approximately 2.

*Time of full bloom*.—Medium for area of Southern San Joaquin Valley, Calif. Approximately May 2nd.

FRUIT

General:

*Ripening period*.—Very early, beginning about June 29th in the area of Southern San Joaquin Valley, Calif.

*Use*.—Fresh market.

*Storage quality*.—Excellent.

Cluster:

*Form*.—Conical, shouldered.

*Cluster size* (*peduncle excluded*).—Large, approximately 700 g.

*Cluster length* (*peduncle excluded*).—Approximately 19 cm.

*Cluster width*.—Approximately 15 cm.

*Cluster weight*.—Approximately 700 g.

*Cluster density*.—Loose-full. Rachis not visible but berries freely moving.

*Number of berries*.—Approximately 140 before trimming.

Peduncle:

*Length*.—Medium, approximately 2.2 cm.

*Diameter*.—Approximately 6 mm.

*Lignification of peduncle*.—Weak.

*Color*.—About Medium Yellow-Green 146C.

Berry:

*Size*.—Large for early season, approximately 7.8 g.

*Dimensions*.—Longitudinal axis: Approximately 27 mm. Horizontal axis: Approximately 21 mm.

*Uniformity of size*.—Uniform.

*Shape*.—Broad elliptic.

*Cross section*.—Circular.

*Skin color* (*without bloom*).—About Dark Red 53B at full ripe, becoming Dark Red-Purple 59A as it becomes past ripe.

*Flesh color*.—About Medium Yellow-Green 148D at full ripe. Dark Red-Purple 59A anthocyanin develops as it becomes past ripe.

*Anthocyanin color of flesh*.—Medium, develops darker throughout the flesh at it becomes past ripe.

*Bloom* (*cuticular wax*).—Medium.

*Pedicel length*.—Approximately 7 mm.

*Pedicel thickness*.—Medium, approximately 1.8 mm.

*Berry separation from pedicel*.—Moderately easy.

*Seed traces*.—Berries contain 1 to 3 rudimentary soft seed traces per berry. Seed traces are about Medium Green 141C.

*Berry firmness*.—Very firm.

*Flesh juiciness*.—Juicy.

*Flesh texture*.—Crisp.

*Particular flavor*.—Slightly fruity aroma.

*Refractometer test*.—About 17-18 Brix.

*Juice ph*.—About 3.8.

*Titratable acidity*.—About 0.41%.

*Brix:acid ratio*.—Approximately 41.5.

Skin:

*Skin thickness*.—Medium, about 175 μm.

*Skin texture*.—Smooth.

*Skin reticulation*.—Absent.

*Skin tenacity*.—Tenacious to flesh.

*Skin tendency to crack*.—Rare.

*Skin sensitivity to sunburn*.—None.

What is claimed is:

1. A new and distinct variety of grapevine as herein illustrated and described.

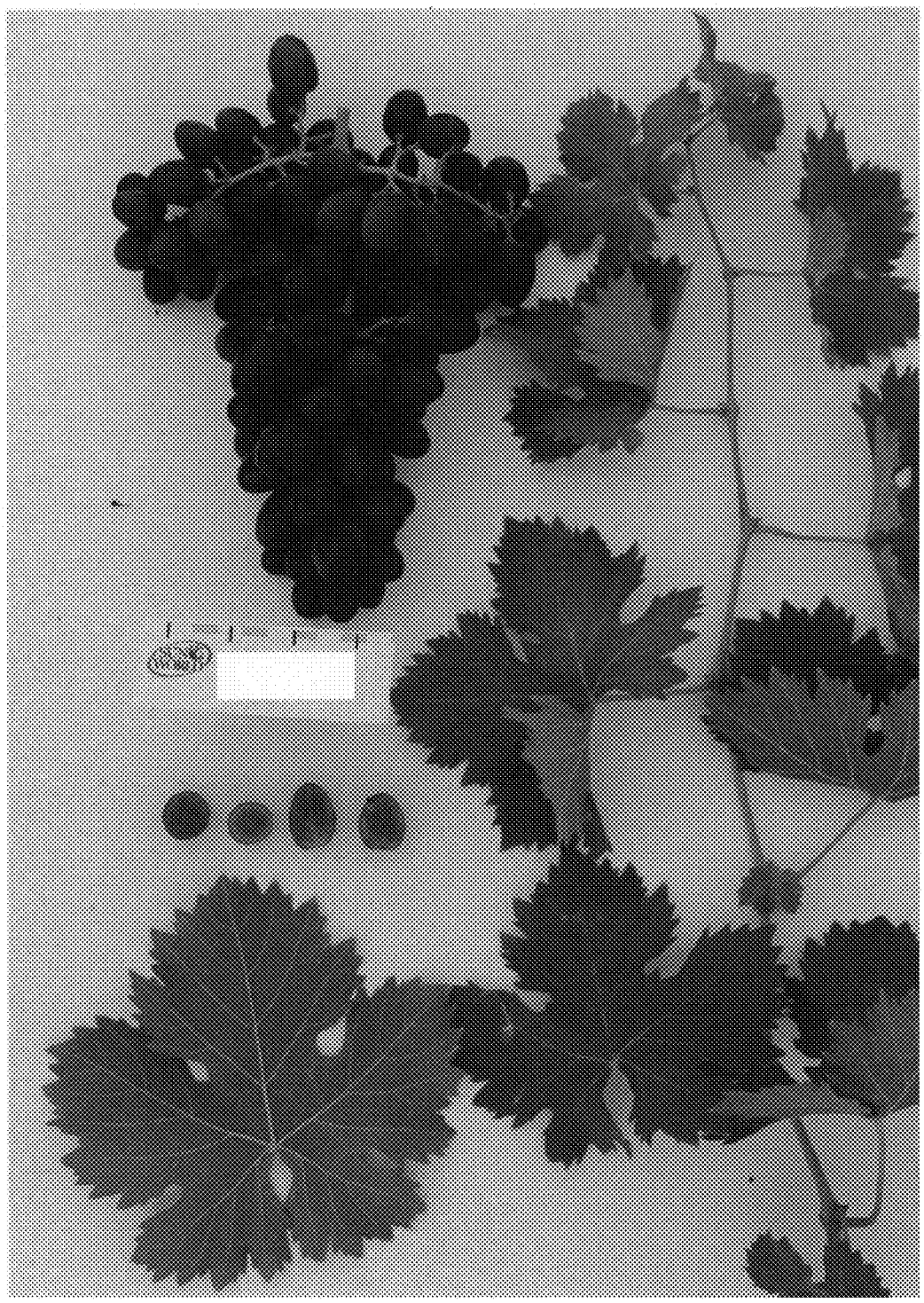

* * * * *